Figure 1:
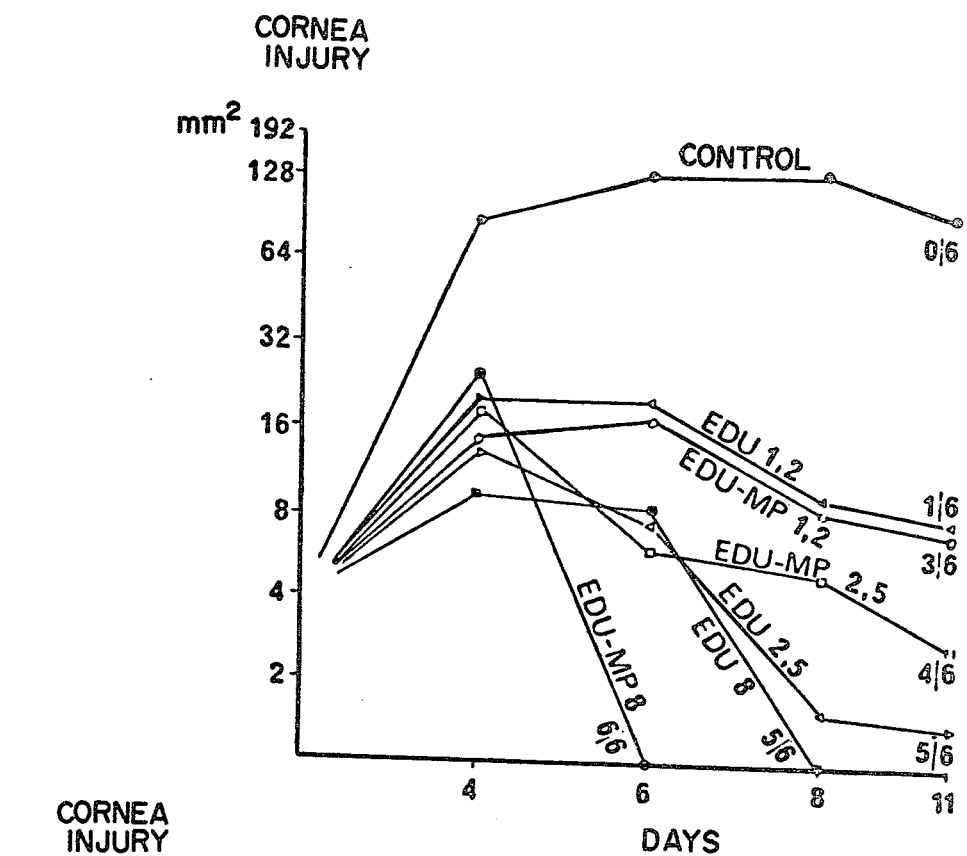

United States Patent [19]

Gauri

[11] 4,271,153
[45] Jun. 2, 1981

[54] NOVEL MONOPHOSPHATES

[75] Inventor: Kailash K. Gauri, Lentföhrden, Fed. Rep. of Germany

[73] Assignee: Robugen GmbH Pharmazeutische Fabrik, Esslingen-Zell, Fed. Rep. of Germany

[21] Appl. No.: 30,852

[22] Filed: Apr. 17, 1979

[30] Foreign Application Priority Data

Sep. 26, 1978 [DE] Fed. Rep. of Germany ....... 2841898

[51] Int. Cl.³ .................... A61K 31/70; C07H 19/10
[52] U.S. Cl. ..................................... 424/180; 536/29
[58] Field of Search .................... 536/23, 29; 424/180

[56] References Cited

U.S. PATENT DOCUMENTS 3,462,416  8/1969  Hanze et al. ............................ 536/23

OTHER PUBLICATIONS

Michelson, A., et al., J. Chem., Soc., 1953, p. 951.
Tener, J.A.C.S., vol. 83, 1961, p. 159.

Primary Examiner—Johnnie R. Brown
Assistant Examiner—Blondel Hazel
Attorney, Agent, or Firm—Hammond & Littell, Weissenberger and Muserlian

[57] ABSTRACT

Novel 5-lower alkyl-2'-desoxyuridine-5'-monophosphates of the formula

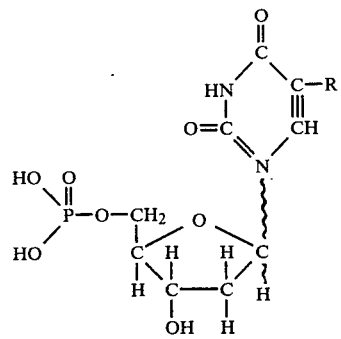

wherein R is lower alkyl of 2 to 6 carbon atoms having antiviral activity.

12 Claims, 3 Drawing Figures

NOVEL MONOPHOSPHATES

STATE OF THE ART

Desoxyuridines having antiviral activity are known and 5-iodo-2'-desoxyuridine (IDU) and 5-ethyl-2'-desoxyuridine (EDU) have been used in the clinical treatment of herpes diseases caused by Herpes Simplex Type 1 and 2 viruses (HSV-1 and HSV-2). Since it is known that 97% of the population have been infected with these herpes viruses with a high percentage experiencing an active infection and with a large proportion tending to suffer reoccurrences, it is of great importance to improve the available drugs. Another factor for the importance of the control of herpes infections caused by HSV-2 is that these viruses have an oncologenic action and are involved in the beginning of some forms of cancer.

OBJECTS OF THE INVENTION

It is an object of the invention to provide the novel monophosphates of formula I and to provide a novel process for their preparation.

It is another object of the invention to provide novel antiviral compositions and to provide a novel method of combatting antiviral infections in warm-blooded animals, especially herpes infections.

These and other objects and advantages of the invention will become obvious from the following detailed description.

THE INVENTION

The novel monophosphates of the invention have the formula

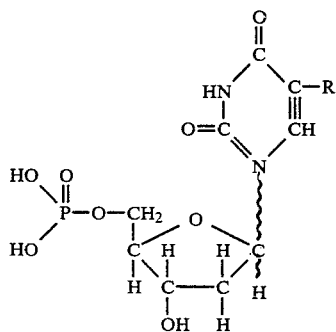

wherein R is lower alkyl of 2 to 6 carbon atoms.

As indicated by the waved lines in the above formula I connecting the nitrogen atom in the 8 position of the uracil residue and a hydrogen atom respectively with the carbon atom in the 1 position of the sugar moiety, the monophosphates of the invention can exist in two anomeric forms. These are the α- and β-anomers, which differ from each other only by the steric arrangement of said uracil residue on carbon atom 1 of the sugar moiety. The invention comprises both the separate α- and β-anomers of the monophosphates of formula I as well as the mixtures thereof.

Examples of suitable alkyls for R are those of 2 to 6 carbon atoms, preferably 2 to 4 carbon atoms such as ethyl, propyl, isopropyl, butyl, isobutyl, pentyl and hexyl.

The novel process of the invention for the preparation of the compounds of formula I comprises reacting a 5-lower alkyl-2'-desoxyuridine with an acetylation agent using the procedure of Michelson et al [J. Chem. Soc., 1953, p. 951] to obtain 5-lower alkyl-3'-acetyl-2'-desoxyuridine, reacting the latter with β-cyanoethyl phosphate by the method of Tener [J.A.C.S., Vol. 83 (1961) p. 159] to obtain 5-lower alkyl-2'-desoxyuridine-5'-monophosphate.

More specifically, the novel process of the invention for the preparation of the compounds of formula I comprises (a) reacting a 5-lower-alkyl-2'-desoxyuridine of the formula

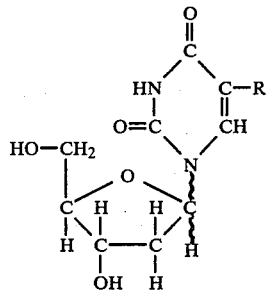

wherein R is as defined above, with a triphenylmethyl halide, preferably triphenylmethyl chloride, in an organic solvent, preferably pyridine, under anhydrous conditions to form the corresponding triphenylmethyl derivative, (b) reacting said triphenylmethyl derivative in an organic solvent, preferably in pyridine, under anhydrous conditions with an acetylating derivative of acetic acid, preferably acetic anhydride, for form an acetylated product, (c) subsequently heating said acetylated product in an organic solvent, preferably acetic acid, to form the corresponding 5-lower alkyl-3'-acetyl-2'-desoxyuridine of the formula

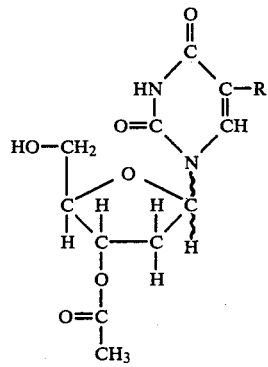

wherein R is as previously defined, (d) reacting the latter product with an organic solution of β-cyanoethyl phosphate, preferably a pyridine solution, in the presence of dicyclohexyl carbodiimide as a condensing agent, (e) removing the cyanoethyl group by mild hydrolysis, preferably mild alkaline hydrolysis, and (f) separating the desired product.

The preparation of the 5-lower alkyl-2'-desoxyuridine starting materials is described in German published patent application No. 1,620,185.

More specifically, the 5-lower alkyl-2'-desoxyuridines are prepared by reacting the corresponding 5- lower alkyl uracils or their mercury salts with the corresponding optionally protected desoxyribose derivative in a manner known per se. For example, the mercury salt of the uracil derivative may be reacted with a protected halogenated desoxy ribose compound. The thus obtained protected 5-lower alkyl uracils are a mixture of the α- and β-anomers. If desired, the two anomeric forms of the protected product may be separated completely or partially by crystallization from various solvents, e.g. toluene or diethyl ether. Thereafter the protective group is selectively cleaved off, e.g. with sodium methylate or methanolic ammonia, in a known manner.

The separated α- and β-anomers of the 5-lower alkyl-2'-desoxyuridines as starting materials of the present process yield the corresponding α- and β-anomer forms respectively of the 5-lower alkyl-2'-desoxyuridine-5'-monophosphates of the invention, whereas a mixture of the α- and β-anomers of the starting 5-lower alkyl-2'-desoxyuridines yields a corresponding α- and β-anomer mixture of the desired end product.

The compounds for the preparation of the starting materials are either known or may be readily prepared by known processes.

The novel antiviral compositions of the invention are comprised of an antivirally effective amount of at least one compound of formula I and an inert pharmaceutical carrier or excipient. The compositions may be in the form of tablets, coated tablets, dragees, gelules, granules, suppositories and injectable solutions or suspensions and may contain one or more other antiviral agents.

Examples of suitable excipients are talc, lactose, starch, magnesium stearate, cocoa butter, aqueous and nonaqueous vehicles, fatty bodies of animal or vegetable origin, paraffinic derivatives, glycols, diverse wetting agents, dispersants or emulsifiers and preservatives.

The compositions are useful for combatting viral infections, especially those of the herpes type such as HSV-1 and HSV-2. The compositions have been found to have antiviral activity against herpes which is clearly superior to 5-ethyl-2'-desoxyuridine (EDU) and are effective against EDU-resistant viruses.

The α-anomer of 5-ethyl-2'-desoxyuridine-5'-monophosphate exhibits an additional, surprising property in that it inhibits the reproduction of Herpes Simplex Viruses. In tissue cultures of chicken embryo fiberblasts this compound significantly inhibits the virus reproduction at a concentration of 10 μg/ml. Under the same conditions the α-anomer of 5-ethyl-2'-desoxyuridine is ineffective. Further, the α-anomer of 5-ethyl-2'-desoxyuridine-5'-monophosphate surprisingly has virostatic activities, but surprisingly is not built into the desoxyribonucleic acid (DNS), which completely rules out any potential genetic risk.

The novel method of preventing or treating viral infections in warm-blooded animals, including humans, comprises administering to warm-blooded animals an antivirally effective amount of at least one compound of formula I. The compounds may be administered orally, rectally, or parenterally and the usual daily dose is 5 to 300 mg/kg depending upon the compound and method of administration. The method is particularly effective against herpes viruses.

In the following examples there are described several preferred embodiments to illustrate the invention. However, it should be understood that the invention is not intended to be limited to the specific embodiments.

PREPARATION OF THE STARTING COMPOUNDS

Preparation A

5-Ethyl-2'-desoxyuridine 0.01 moles mono-(5-ethyluracilyl)mercury and 0.02 moles di-p-chlorobenzoyl-desoxyribofuranosyl chloride are heated under stirring in 150 ml anhydrous toluene until reflux temperature, forming a clear solution. After distilling off the toluene the residue is taken up in 100 ml chloroform and shaken with 30% potassium iodide solution to eliminate the mercury ions. Petrol ether with boiling point 50° to 70° C. is added to the organic phase and the crystallized product is filtered off.

Thereafter the product is kept under reflux with a 2% sodiummethylate solution in absolute methanol for two hours to desacylate. After distilling off the methanol the residue is treated with a cation exchanger in aqueous solution to eliminate the sodium ions. The mixture is extracted with diethylether and the aqueous solution is evaporated to dryness under vacuum. 5-ethyl-2'-desoxyuridine with melting point 154° to 157° C. is obtained.

| Elemental analysis $C_{11}H_{16}N_2O_5$ | | M.W. 256.26 | |
|---|---|---|---|
| | C | H | N |
| calc.: | 51.55 | 6.29 | 10.93% |
| found: | 51.32 | 6.41 | 10.53% |

Preparation B

5-Ethyl-2'-desoxyuridine (alternate procedure)

1.8 g mono-(5-ethyluracilyl)-mercury are heated in 70 ml absolute toluene under stirring and with a bath temperature of approximately 130° C. for about 1 hour using a water separator. During this time approximately 22 ml toluene are distilled off.

The mixture is allowed to cool and 4.0 g 3,5-di-p-tolyl-2-desoxy-D-ribofuranosyl chloride are added. Thereafter the heating is continued for another 40 minutes, during which time approximately 8.5 ml toluene are distilled off.

After cooling the insolubles are sucked off, the filtrate is treated with 30 ml of a 15% aqueous potassium iodide solution, the layers are separated and the organic layer is washed with 20 ml of water. After repeating the separation the toluene layer is dried over a drying agent. After standing over night, the drying agent is filtered off, washed with little absolute diethylether and to the filtrate approximately 60 ml n-hexane are added until the solution becomes permanently cloudy. The mixture is allowed to stand over night at room temperature and thereafter 5 hours in a deep freezer.

The formed precipitate is sucked off, washed with n-hexane and finally dried in a vacuum desiccator. Yield: 1.15 g light brownish crystals with melting point 195° to 197° C. The filtrate is additioned with another 120 ml n-hexane and after standing for 3 days the initially oily precipitate is sucked off. It is washed with n-hexane and dried in a vacuum desiccator.

Yield: 0.62 g slightly brownish crystals with melting point 120° to 175° C. These are a mixture of two substances, as evidenced by thin layer chromatography using benzene:chloroform:acetone 5:4:1 on silicagel as the carrier.

The initially precipitated reaction product (1.15 g) is nearly pure according to chromatography. For further purification it is recrystallized from 180 ml ethanol with activated charcoal additioned with some cellulose. The mixture is allowed to stand in the deep freezer over night, the formed precipitate is sucked off and dried in a vacuum desiccator.

Yield: 1.05 g colourless crystals with melting point 198° C.

| Elemental analysis $C_{27}H_{28}N_2O_7$ | | M.W. 492.54 | |
| --- | --- | --- | --- |
| | C | H | N |
| calc.: | 64.83 | 5.73 | 5.68% |
| found: | 65.59 | 5.53 | 5.41% |

Based on NMR spectroscopic investigation the product consists of the β-anomer.

To 1 g of the above compound in 20 to 30 ml of absolute methanol 3 to 5 ml of a 1 N sodium methylate solution is added and the mixture is heated under reflux and under anhydrous conditions for approximately 1 hour. After completion of the reaction the methanol is distilled off in vacuo and the residue is additioned with approximately 7 ml of water. By adding a cation exchanger resin (H-form) and short shaking the solution is neutralized and after filtration the neutral, colourless solution is evaporated to dryness under vacuum. The residue is taken up in 20 to 25 ml of water, extracted 3 times with 5 ml each of methylen chloride and concentrated again in vacuo. The obtained crude nucleoside is dried again by azeotropic distillation with benzene/absolute ethanol. Thereafter the product is crystallized by adding absolute diethylether.

Yield: 0.3 g product with melting point 156° C.

The α-anomer has a melting point of 178° C.

Preparation C

5-Propyl-2'-desoxyuridine

To a solution of 15,4 g 5-propyluracil (0.1 mole) and 21,7 g trimethylsilyl chloride (0,2 mole) in 250 ml anhydrous benzene 20.2 g dry triethylamine (0,2 mole) are added dropwise under stirring and exclusion of humidity within a time span of 15 minutes. After further stirring for about 12 hours the unreacted 5-propyl-uracil and the precipitated dry ethylamine hydrochloride are separated and the filtrate is concentrated under vacuum. The residue is dissolved in 150 ml of absolute toluene and under stirring a solution of 43 g 3,5-di-(p-chlorobenzoyl)-2-desoxy-D-ribofuranosyl chloride (0,1 mole) in 500 ml toluene and thereafter 31,8 g mercury (II)-acetate are added and the stirring is continued another 24 hours. After filtration the filtrate is extracted with a 30% aqueous potassium iodide solution and thereafter washed with water. After drying over sodium sulfate the toluene solution is concentrated to approximately 100 ml. Upon standing the protected nucleoside crystallizes. 45 g of a product with melting point 140°–165° C. are obtained.

Yield: 82% of the theoretical yield.

This product is a mixture of the p-chlorobenzoyl-protected α- and β-anomers. After one crystallization from toluene 28 g of a product are obtained which melts completely at 184° C. This substance consists of approximately 90% β-anomer. By further recrystallization no complete separation from the α-nucleoside could be achieved.

The combined toluene filtrates are concentrated under vacuum to a sirupy consistency and thereafter additioned with approximately 150 ml ether. After prolonged standing in a refrigerator a second crop of 14 g of the anomer mixture with melting point 135°–154° C. are obtained.

Upon recrystallization with ether the α-anomer with melting point 139°–142° C. is obtained.

According to thin layer chromatography this product still contains some β-product.

5,47 g of the above β-product melting at 184° C. are additioned with a solution of 3 ml of a 2% sodium methylate solution in 100 ml methanol and the mixture is heated under reflux for 90 minutes. Further work-up according to preparation A yields 2,0 g propyldesoxyuridine with melting point 162°–163° C.

In the UV-spectrum the maximum (266 μm) is shifted neither in alkaline nor in acidic medium. This confirms that the substituent is on the nitrogen atom at the 3 position.

EXAMPLE 1

5-ethyl-2'-desoxyuridine-5-monophosphate 2 g of 5-ethyl-2'-desoxyuridine were reacted with triphenylmethyl chloride to obtain 4.1 g (75% yield) of the corresponding triphenylethyl derivative melting at 180° C. which was then reacted with acetic anhydride to obtain 1.8 g (75% yield) of 5-ethyl-3'-acetyl-2'-desoxyuridine melting at 150° C. which was analytically pure.

A mixture of 0.3 g (0,001 mole) of 5-ethyl-3'-acetyl-2'-desoxyuridine, 1.2 g of dicyclohexylcarbodiimide and 2 ml of a pyridine solution of 0.002 mole of β-cyanoethyl phosphate were reacted to obtain 200 mg (62% yield) of 5-ethyl-2'-desoxyuridine-5'-monophosphate with an Rf=0.17 [1-7-2 ammonia-isopropanol-water mixture].

U.V. Spectrum: pH=3.8 $\lambda_{min}$ 234, e=1745; pH=3 $\lambda_{max}$267, e=7755.

Using the same procedure, the 5-monophosphates of 5-propyl-2'-desoxyuridine, 5-butyl-2'-desoxyuridine, 5-pentyl-2'-desoxyuridine and 5-hexyl-2'-desoxyuridine were prepared.

EXAMPLE 2

A gel was prepared containing 1 g of polyacrylic acid, 2 g of 5-ethyl-2'-desoxyuridine-5'-monophosphate, 2 mg of sodium ethyl mercuric thiosalicylate, sufficient sodium hydroxide for a pH of 7 and sufficient demineralized water for a final weight of 100 g.

A second gel was prepared containing 2 g of methylcellulose, 1 g of 5-propyl-2'-desoxyuridine-5'-monophosphate, 0.01 g of benzalkonium chloride, 0.1 g of sodium ethylenediaminetetraacetate and sufficient demineralized water for a final weight of 100 g.

The preferred compositions of the invention are in the form of aqueous solutions, ointments, or gels containing 0.1 to 15% by weight, preferably 0.1 to 10%, of the active compound of formula I. Suitable thickening agents are carboxymethylcellulose, polyvinylpyrrolidone or polyacrylic acid.

PHARMACOLOGICAL DATA

A. Antiviral Activity

The antiviral activity of 5-ethyl-2'-desoxyuridine-5'-monophosphate and 5-ethyl-2'-desoxyuridine was compared with 7 groups of six rabbits. The right cornea of each rabbit was scratched and was infected with Herpes Simplex Virus Type 1. Three groups of rabbits were treated with 5-ethyl-2'-desoxyuridine (EDU) at concentrations of 1.2, 2.5 and 8% while 3 other groups were treated with 5-ethyl-2'-desoxyuridine-5'-monophosphate (EDU-MP) at concentrations of 1.2, 2.5 and 8%. The seventh group served as a control group and the results are reported in FIG. 1.

The results of FIG. 1 clearly show the superior antiviral activity of the monophosphate of the invention since on the sixth day the corneas of all the rabbits treated with the 8% concentration of EDU-MP were healed after 6 days while with the rabbits treated with the 8% concentration of EDU, only the cornea of 5 out of 6 rabbits were healed after 8 days.

Figure 2:
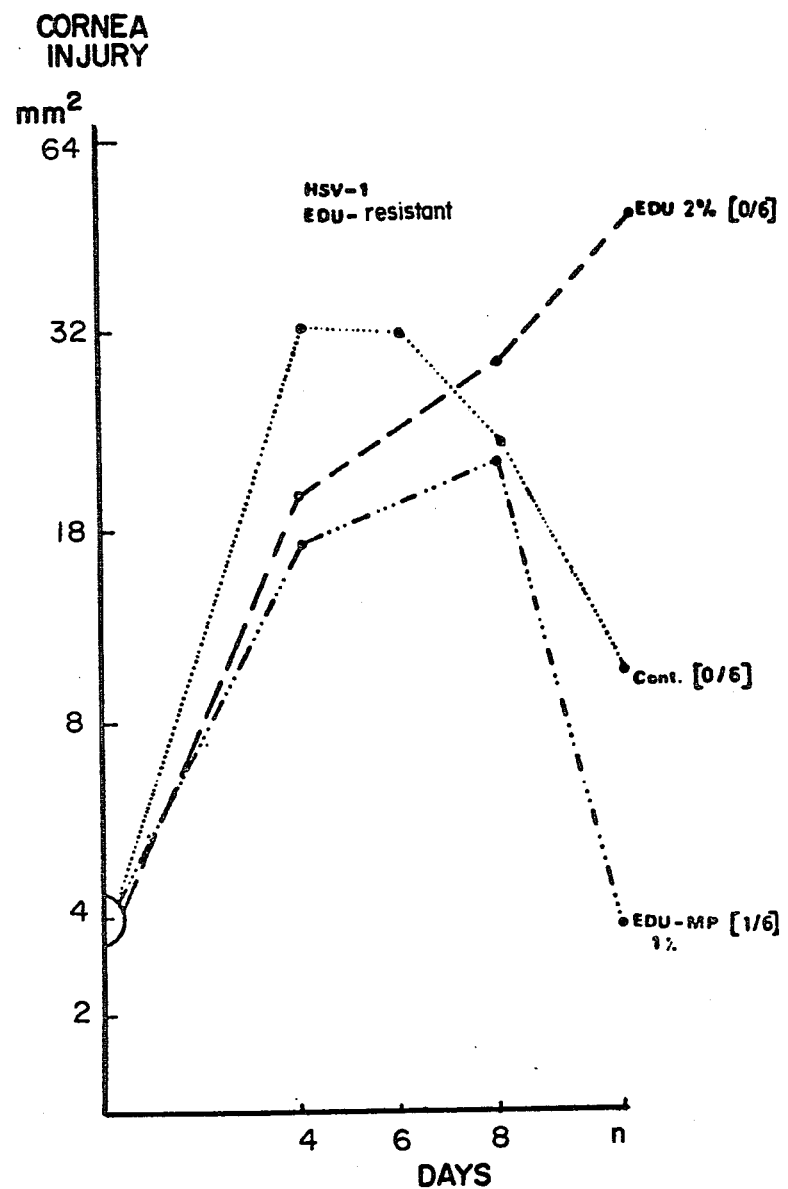

To demonstrate the superiority of EDU-MP over EDU with EDU resistant viruses, the above test was repeated with three sets of 6 rabbits, one set as controls and one set treated with a solution of 2% of EDU and a third set treated with a solution of 1% of EDU-MP and the results are reported in FIG. 2. The results of FIG. 2 show that with progressive treatment of the infected rabbit cornea with the 1% concentration of EDU-MP, there is a strong inhibition of the infection while the infection progresses when treated with a 2% concentration of EDU under the same conditions.

B. Cornea Compatibility

Figure 3:
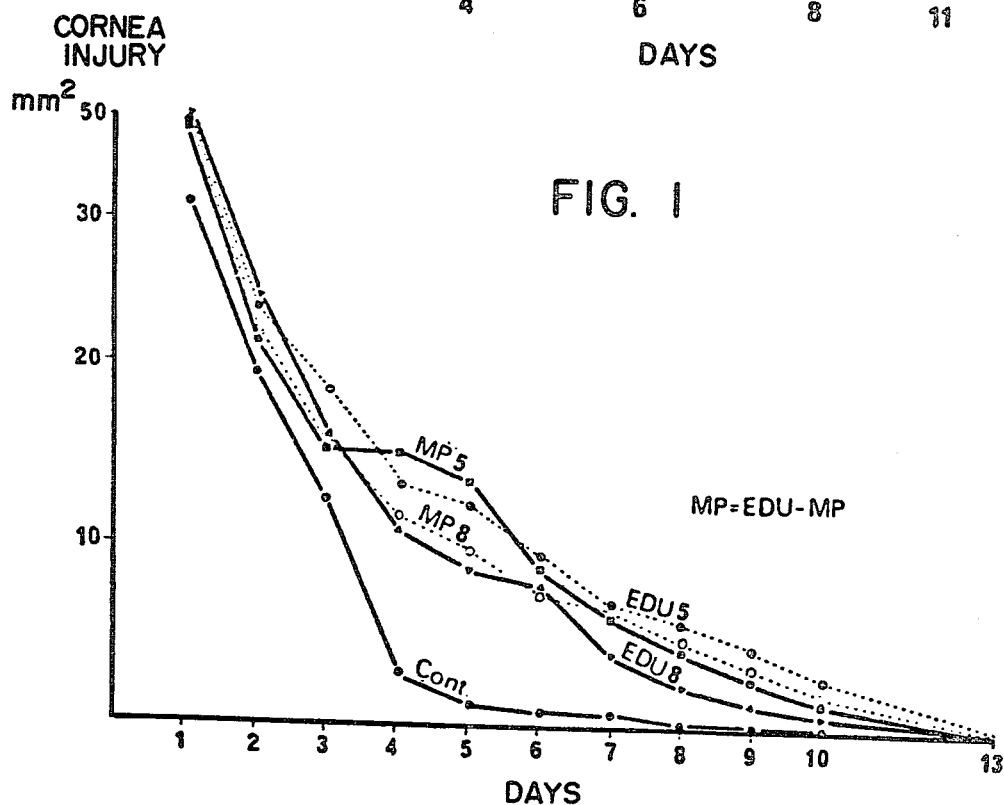

To demonstrate the compatibility of EDU and EDU-MP with rabbit cornea, a wound of 50 mm² was produced on the cornea of test rabbits and the process of the healing was determined by the reduction in size of cornea damage over a period of 11 days. Control rabbits received a daily treatment with just a solution of 0.90% sodium chloride while the test rabbits received a daily treatment with a solution containing 5% or 8% of EDU or EDU-MP and the results are shown in FIG. 3.

In all cases, the healing process was completed no later than the 13th day. Treatment with EDU monophosphate did not substantially interfer with the healing process while the EDU treatment appeared to slow the healing process somewhat.

Various modifications of the products and processes of the invention may be made without departing from the spirit or scope thereof and it is to be understood that the invention is intended to be limited only as defined in the appended claims.

I claim:

1. A compound of the formula

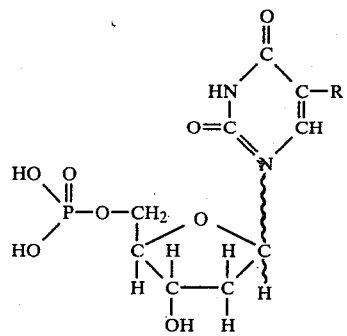

wherein R is lower alkyl of 2 to 6 carbon atoms.

2. A compound of claim 1 which is 5-ethyl-2'-desoxyuridine-5'-monophosphate.

3. The α-anomer of the compound of claim 2.

4. A compound of claim 1 which is 5-propyl-2'-desoxyuridine-5-monophosphate.

5. A composition for combatting herpes viral infections comprising an antivirally effective amount of at least one compound of claim 1 and an excipient.

6. A composition of claim 5 wherein the compound is 5-ethyl-2'-desoxyuridine-5'-monophosphate.

7. A composition of claim 6, wherein the compound is the α-anomer of 5-ethyl-2'-desoxyuridine-5'-monophosphate.

8. A composition of claim 5, wherein the compound is 5-propyl-2'-desoxyuridine-5'-monophosphate.

9. A method of preventing or treating herpes viral infections in warm-blooded animals comprising administering to warm-blooded animals an herpes antivirally effective amount of at least one compound of claim 1.

10. The method of claim 9 wherein the compound is 5-ethyl-2'-desoxyuridine-monophosphate.

11. The method of claim 9 wherein the compound is the α-anomer of 5-ethyl-2'-desoxyuridine monophosphate.

12. The method of claim 9 wherein the compound is 5-propyl-2'-desoxyuridine monophosphate.

* * * * *

UNITED STATES PATENT AND TRADEMARK OFFICE
CERTIFICATE OF CORRECTION

PATENT NO. : 4,271,153
DATED : June 2, 1981
INVENTOR(S) : KAILASH K. GAURI

It is certified that error appears in the above—identified patent and that said Letters Patent is hereby corrected as shown below:

Abstract, and Column 1, structural formula:

The portion of the structural formula which reads

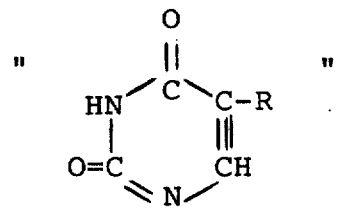

should read -- 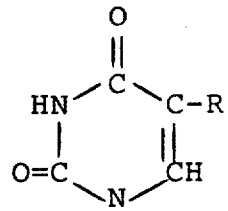 -- .

Signed and Sealed this

Twentieth Day of October 1981

[SEAL]

Attest:

Attesting Officer

GERALD J. MOSSINGHOFF

Commissioner of Patents and Trademarks